US006225322B1

(12) United States Patent
Cooper et al.

(10) Patent No.: US 6,225,322 B1
(45) Date of Patent: *May 1, 2001

(54) COMPOUNDS USEFUL FOR INHIBITION OF FARNESYL PROTEIN TRANSFERASE

(75) Inventors: Alan B. Cooper, West Caldwell; Jagdish A. Desai, Spotswood; Anil K. Saksena, Upper Montclair; Viyyoor M. Girijavallabhan, Parsippany; James J-S Wang, Westfield, all of NJ (US)

(73) Assignee: Schering Corporation, Kenilworth, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/094,688

(22) Filed: Jun. 15, 1998

Related U.S. Application Data

(60) Provisional application No. 60/049,855, filed on Jun. 17, 1997.

(51) Int. Cl.[7] ............... A61K 31/4545; A61K 31/4375; C07D 401/14; C07D 471/04; A61P 35/00

(52) U.S. Cl. ............................... 514/291; 546/81

(58) Field of Search ............................... 546/81; 514/291

(56) References Cited

U.S. PATENT DOCUMENTS

| 5,089,496 | * | 2/1992 | Piwinski ........................... 514/253 |
| 5,696,121 | * | 12/1997 | Bishop ............................... 514/254 |
| 5,714,609 | | 2/1998 | Doll . |
| 5,719,148 | * | 2/1998 | Bishop ............................. 514/228.2 |
| 5,801,175 | | 9/1998 | Afonso . |
| 5,807,853 | * | 9/1998 | Bishop ............................. 514/228.2 |
| 5,958,890 | | 9/1999 | Rane et al. . |

FOREIGN PATENT DOCUMENTS

| 339978 | * | 11/1989 | (EP) . |
| WO 95 10515 | | 4/1995 | (WO) . |
| WO 95 10516 | | 4/1995 | (WO) . |
| WO 96 30363 | | 10/1996 | (WO) . |
| WO 96 31477 | | 10/1996 | (WO) . |
| WO 96 31478 | | 10/1996 | (WO) . |
| WO 96 31505 | | 10/1996 | (WO) . |
| WO 97 23478 | | 7/1997 | (WO) . |

OTHER PUBLICATIONS

Khosarvi–Far et al. Cell Growth & Differentiation. 3, 461–9, Jul. 1992.*
King FD. Medicinal Chemistry. Principles and Practice. The Royal Society of Chemistry. pp. 206–209, 1994.*
Bishop W. R. et al., XP002050604, *Journal of Biological Chemistry*, "Novel Tricyclic Inhibitors . . . ", vol. 270, No. 51, pp. 30611–30618 (1995).

Njoroge F.G. et al., XP002056550, *Bioorganic & Medicinal Chemistry Letters*, "Novel Tricyclic Aminoacetyl . . . ", vol. 6, No. 24, pp. 2977–2982 (1996).

Buss J. E. et al., XP002056549, *Chemistry and Biology*, "Farnesyl Transferase Inhibitors: . . . ", vol. 118, No. 2, pp. 787–791 (1995).

Njoroge F. G. et al., XP002056551, *Bioorganic & Medicinal Chemistry*, "Discovery of Novel Nonpeptide . . . ", vol. 5, No. 1, p. 101–113 (1997).

Samuel L. Graham, *Exp. Opin. Ther. Patents*, vol. 5(12), pp. 1269–1285 (1995).

\* cited by examiner

*Primary Examiner*—Evelyn Mei Huang
(74) *Attorney, Agent, or Firm*—Arthur Mann; Allan N. Kutzenco

(57) ABSTRACT

Novel compounds of formula

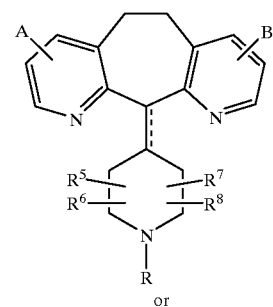

(1.0)

or

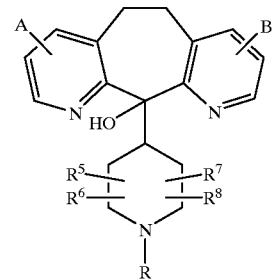

(2.0)

are disclosed. Also disclosed is a method of inhibiting farnesyl protein transferase function and therefore inhibiting the abnormal growth of cells. The method comprises administering a compound of the above formula to a biological system. In particular, the method inhibits the abnormal growth of cells in a mammal such as a human being. Also disclosed is a method of effecting an anti-allergic response by administering the compounds.

20 Claims, No Drawings

COMPOUNDS USEFUL FOR INHIBITION OF FARNESYL PROTEIN TRANSFERASE

This application claims the benefit of U.S. Provisional application No. 60/049,855, filed Jun. 17, 1997.

BACKGROUND

WO 95/10516, published Apr. 20, 1995 discloses tricyclic compounds useful for inhibiting farnesyl protein transferase.

In view of the current interest in inhibitors of farnesyl protein transferase, a welcome contribution to the art would be compounds useful for the inhibition of farnesyl protein transferase. Such a contribution is provided by this invention.

SUMMARY OF THE INVENTION

This invention provides compounds useful for the inhibition of farnesyl protein transferase (FPT). The compounds of this invention are represented by the formula:

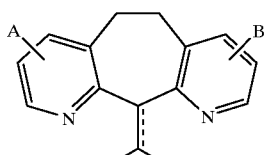

(1.0)

or

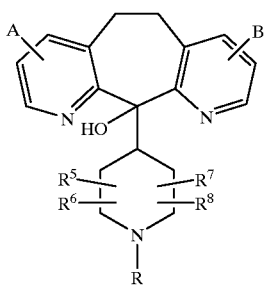

(2.0)

or a pharmaceutically acceptable salt or solvate thereof, wherein:

A is alkyl, halo or H;

B is methyl, halo or H;

the dotted line represents an optional double bond;

$R^5$, $R^6$, $R^7$ and $R^8$ are independently selected from the group consisting of H, —$CF_3$, —$COR^{10}$, alkyl or aryl, said alkyl or aryl optionally being substituted with —$OR^{10}$, —$SR^{10}$, —$S(O)_tR^{11}$, —$NR^{10}COOR^{11}$, —$N(R^{10})_2$, —$NO_2$, —$COR^{10}$, —$OCOR^{10}$, —$OCO_2R^{11}$, —$CO_2R^{10}$, $OPO_3R^{10}$ or $R^5$ is combined with $R^6$ to represent =O or =S and/or $R^7$ is combined with $R^8$ to represent =O or =S;

$R^{10}$ represents H, alkyl, aryl, or aralkyl (e.g., benzyl);

$R^{11}$ represents alkyl or aryl;

R is —$C(O)R^1$, —$C(O)$-$OR^1$, —$C(O)NR^1R^2$, —$S(O)_2$-$R^1$, or —$S(O)_2NR^1R^2$ wherein $R^1$ and $R^2$ are independently selected from the group consisting of H, alkyl, aryl, arylalkyl, heteroaryl, heteroarylalkyl, C3–C6 cycloalkyl, cycloalkylalkyl, heterocycloalkyl, substituted alkyl, substituted aryl, substituted arylalkyl, substituted heteroaryl, substituted heteroarylalkyl, substituted (C3–C6) cycloalkyl, substituted cycloalkylalkyl, substituted heterocycloalkyl, wherein said substituted groups have one or more substituents selected from: $C_1$–$C_6$ alkyl, alkoxy, aralkyl, heteroarylalkyl, —$NO_2$, alkyloxyalkyl, alkyloxyalkyloxyalkyl, $C_3$–$C_6$ cycloalkyl, aryl, —CN, heteroaryl, heterocycloalkyl, =O, —OH, amino, substituted amino, nitro and halo, with the proviso that $R^1$ is not H for —C(O)—$OR^1$ or for —$S(O)^2R^1$.

The compounds of this invention: (i) potently inhibit farnesyl protein transferase, but not geranylgeranyl protein transferase I, in vitro; (ii) block the phenotypic change induced by a form of transforming Ras which is a farnesyl acceptor but not by a form of transforming Ras engineered to be a geranylgeranyl acceptor; (iii) block intracellular processing of Ras which is a farnesyl acceptor but not of Ras engineered to be a geranylgeranyl acceptor; and (iv) block abnormal cell growth in culture induced by transforming Ras.

The compounds of this invention inhibit farnesyl protein transferase and the farnesylation of the oncogene protein Ras. Thus, this invention further provides a method of inhibiting farnesyl protein transferase, (e.g., ras farnesyl protein transferase) in mammals, especially humans, by the administration of an effective amount of the tricyclic compounds described above. The administration of the compounds of this invention to patients, to inhibit farnesyl protein transferase, is useful in the treatment of the cancers described below.

This invention provides a method for inhibiting or treating the abnormal growth of cells, including transformed cells, by administering an effective amount of a compound of this invention. Abnormal growth of cells refers to cell growth independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; and (3) benign and malignant cells of other proliferative diseases in which aberrant Ras activation occurs.

This invention also provides a method for inhibiting or treating tumor growth by administering an effective amount of the tricyclic compounds, described herein, to a mammal (e.g., a human) in need of such treatment. In particular, this invention provides a method for inhibiting or treating the growth of tumors expressing an activated Ras oncogene by the administration of an effective amount of the above described compounds. Examples of tumors which may be inhibited or treated include, but are not limited to, lung cancer (e.g., lung adenocarcinoma), pancreatic cancers (e.g., pancreatic carcinoma such as, for example, exocrine pancreatic carcinoma), colon cancers (e.g., colorectal carcinomas, such as, for example, colon adenocarcinoma and colon adenoma), myeloid leukemias (for example, acute myelogenous leukemia (AML)), thyroid follicular cancer, myelodysplastic syndrome (MDS), bladder carcinoma, epidermal carcinoma, breast cancer and prostate cancer.

It is believed that this invention also provides a method for inhibiting or treating proliferative diseases, both benign and malignant, wherein Ras proteins are aberrantly activated as a result of oncogenic mutation in other genes—i.e., the Ras gene itself is not activated by mutation to an oncogenic form—with said inhibition or treatment being accomplished by the administration of an effective amount of the tricyclic compounds described herein, to a mammal (e.g., a human) in need of such treatment. For example, the benign proliferative disorder neurofibromatosis, or tumors in which Ras is activated due to mutation or overexpression of tyrosine kinase oncogenes (e.g., neu, src, abl, lck, and fyn), may be inhibited or treated by the tricyclic compounds described herein.

The tricyclic compounds useful in the methods of this invention inhibit or treat the abnormal growth of cells. Without wishing to be bound by theory, it is believed that these compounds may function through the inhibition of G-protein function, such as ras p21, by blocking G-protein isoprenylation, thus making them useful in the treatment of proliferative diseases such as tumor growth and cancer. Without wishing to be bound by theory, it is believed that these compounds inhibit ras farnesyl protein transferase, and thus show antiproliferative activity against ras transformed cells.

DETAILED DESCRIPTION OF THE INVENTION

As used herein, the following terms are used as defined below unless otherwise indicated:

MH$^+$—represents the molecular ion plus hydrogen of the molecule in the mass spectrum;

Bu—represents butyl;
Et—represents ethyl;
Me—represents methyl;
Ph—represents phenyl;
benzotriazol-1-yloxy represents

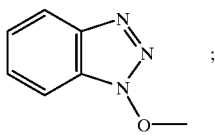

1-methyl-tetrazol-5-ylthio represents

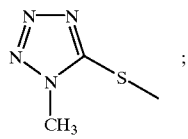

alkyl—(including the alkyl portions of alkoxy, alkylamino and dialkylamino)—represents straight and branched carbon chains and contains from one to twenty carbon atoms, preferably one to six carbon atoms;

alkanediyl—represents a divalent, straight or branched hydrocarbon chain having from 1 to 20 carbon atoms, preferably 1 to 6 carbon atoms, the two available bonds being from the same or different carbon atoms thereof, e.g., methylene, ethylene, ethylidene,
—CH$_2$CH$_2$CH$_2$—, —CH$_2$CHCH$_3$, —CHCH$_2$CH$_3$, etc.

cycloalkyl—represents saturated carbocyclic rings branched or unbranched of from 3 to 20 carbon atoms, preferably 3 to 7 carbon atoms;

heterocycloalkyl—represents a saturated, branched or unbranched carbocylic ring containing from 3 to 15 carbon atoms, preferably from 4 to 6 carbon atoms, which carbocyclic ring is interrupted by 1 to 3 hetero groups selected from —O—, —S— or —NR$^{10}$-(suitable heterocycloalkyl groups including 2- or 3-tetrahydrofuranyl, 2- or 3-tetrahydrothienyl, 2-, 3- or 4-piperidinyl, 2- or 3-pyrrolidinyl, 2- or 3-piperizinyl, 2- or 4-dioxanyl, etc.);

alkenyl—represents straight and branched carbon chains having at least one carbon to carbon double bond and containing from 2 to 12 carbon atoms, preferably from 2 to 6 carbon atoms and most preferably from 3 to 6 carbon atoms;

alkynyl—represents straight and branched carbon chains having at least one carbon to carbon triple bond and containing from 2 to 12 carbon atoms, preferably from 2 to 6 carbon atoms;

aryl (including the aryl portion of aryloxy and aralkyl)—represents a carbocyclic group containing from 6 to 15 carbon atoms and having at least one aromatic ring (e.g., aryl is a phenyl ring), with all available substitutable carbon atoms of the carbocyclic group being intended as possible points of attachment, said carbocyclic group being optionally substituted (e.g., 1 to 3) with one or more of halo, alkyl, hydroxy, alkoxy, phenoxy, CF$_3$, amino, alkylamino, dialkylamino, —COOR$^{10}$ or —NO$_2$; and halo-represents fluoro, chloro, bromo and iodo; and heteroaryl-represents cyclic groups, optionally substituted with R$^3$ and R$^4$, having at least one heteroatom selected from O, S or N, said heteroatom interrupting a carbocyclic ring structure and having a sufficient number of delocalized pi electrons to provide aromatic character, with the aromatic heterocyclic groups preferably containing from 2 to 14 carbon atoms, e.g., triazolyl, 2-, 3- or 4-pyridyl or pyridyl N-oxide (optionally substituted with R$^3$ and R$^4$), wherein pyridyl N-oxide can be represented as:

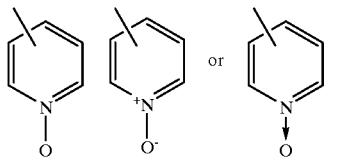

The following solvents and reagents are referred to herein by the abbreviations indicated: tetrahydrofuran (THF); ethanol (EtOH); methanol (MeOH); acetic acid (HOAc or AcOH); ethyl acetate (EtOAc); N,N-dimethylformamide (DMF); trifluoroacetic acid (TFA); trifluoroacetic anhydride (TFAA); 1-hydroxybenzotriazole (HOBT); m-chloroperbenzoic acid (MCPBA); triethylamine (Et$_3$N); diethyl ether (Et$_2$O); ethyl chloroformate (ClCO$_2$Et); and 1-(3-dimethylaminopropyl)-3-ethyl carbodiimide hydrochloride (DEC).

Representative compounds of Formula 1.0 and 2.0 include, but are not limited to:

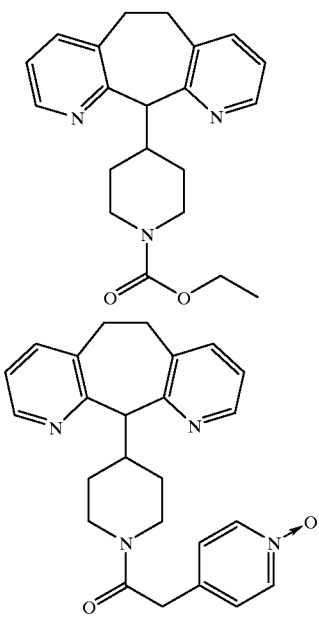

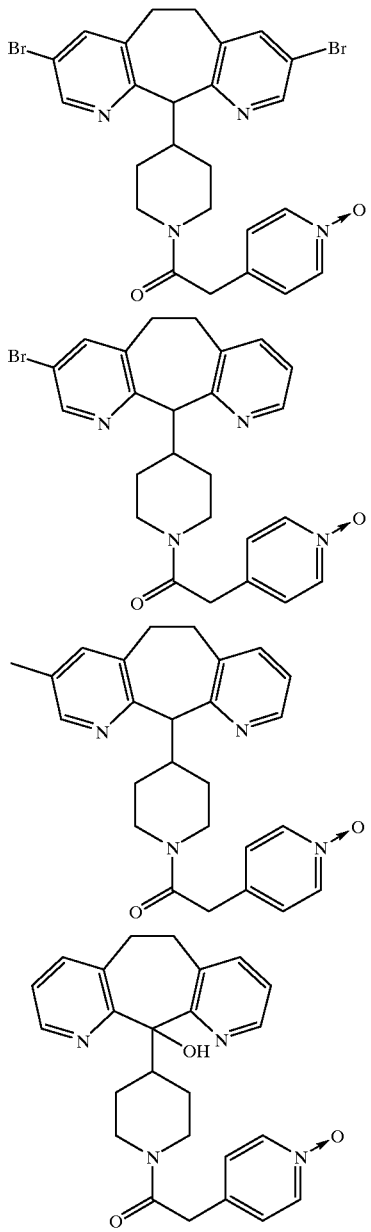

In the compounds of the present invention, A is preferably methyl or halo, more preferably Br. B is preferably methyl or halo, more preferably, Br.

$R^5$, $R^6$, $R^7$ and $R^8$ are preferably selected from the group consisting of H, —$CF_3$, alkyl, aryl, cycloalkyl, and heterocycloalkyl, more preferably $R^5$, $R^6$, $R^7$ and $R^8$ are H.

R is preferably —C(O)$R^1$. Preferably, $R^1$ is —$(CH_2)_nR^A$, wherein n is an integer from 0 to 6, preferably 1 to 3, most preferably, 1, and wherein $R^A$ is selected from aryl, cycloalkyl and heterocycloalkyl. More preferably, $R^A$ is selected from

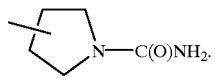

The compounds of the present invention may be made according to the reaction schemes described below from compounds having the formula:

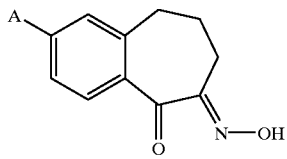

3.0

These ketones can be prepared according to the methods described in J. Med. Chem. 1984, 27, 20–27 (Kaminski, et.al.), the contents of which are fully incorporated herein by reference.

Scheme 1 shows the preparation of Compound (1.0) without the optional double bond. Compound (3.0) is reacted with sodium hydride and allyl bromide in a suitable solvent, e.g., DMF, at a temperature of about 0° C., and stirred at ambient temperature for about 18–24 hours. The product is then recovered by filtration and chromatographed on silica gel to obtain the oxime allylether (compound 3.1). Compound 3.1 is reacted with a grignard reagent (N-methylpiperidine-4-magnesium chloride, substituted with substituents R5, R6, R7, and R8) in a suitable solvent e.g., THF at a temperature of about 0° C. The grignard reagent may be prepared by methods known in the art. The reaction mixture is added to a saturated ammonium chloride solution which is extracted with ethyl acetate. The ethyl acetate layer is filtered and the filtrate is chromatographed on silica gel to obtain compound (3.2). Compound (3.2) is then chlorinated with a chlorinating agent, e.g., thionyl chloride to form comound (3.3). Compound (3.3) can be reacted with zinc in glacial actic acid to remove the chlorine subsitutent. The product is recovered by evaporating the acetic acid under high vacuum, dissolving the residue in a suitable solvent, e.g., methylene chloride, filtering, and chromatographing the filtrate on silica gel to obtain compound (3.4) Compound (3.4) can be cyclized to form a tricyclic ring by placing it in a sealed tube, sealed in the presence of air, and heated to 180° C. for about 7 hours to yield a mixed product (a methyl-substituted tricyclic (compound 3.5) and a tricyclic without the methyl substitutent (compound 3.6)). Compounds 3.5 and 3.6 may be separated by chromatographing the mixed product on silica gel. Depending on whether it is desired for the B substituent of compound (1.0) or (2.0) to be methyl or H, either compound (3.6 or 3.5) is de-methylated by treatment with ethylchloroformate in the presence of a suitable base such as triethyl amine to form compound (3.7). Compound (3.7) is then treated with a suitable acid such as hydrochloric acid under reflux conditions for 5–24 hours and the solvent evaporated and the reaction mixture coupled with a suitable carboxylic acid containing the $R^1$ group using DEC and HOBt coupling conditions known to those skilled in the art to obtain compound (1.0). If compound (2.0) is desired, compound (3.2) can be subjected to the same conditions that compound (3.4) is subjected to and the reaction sequence can proceed as described above.

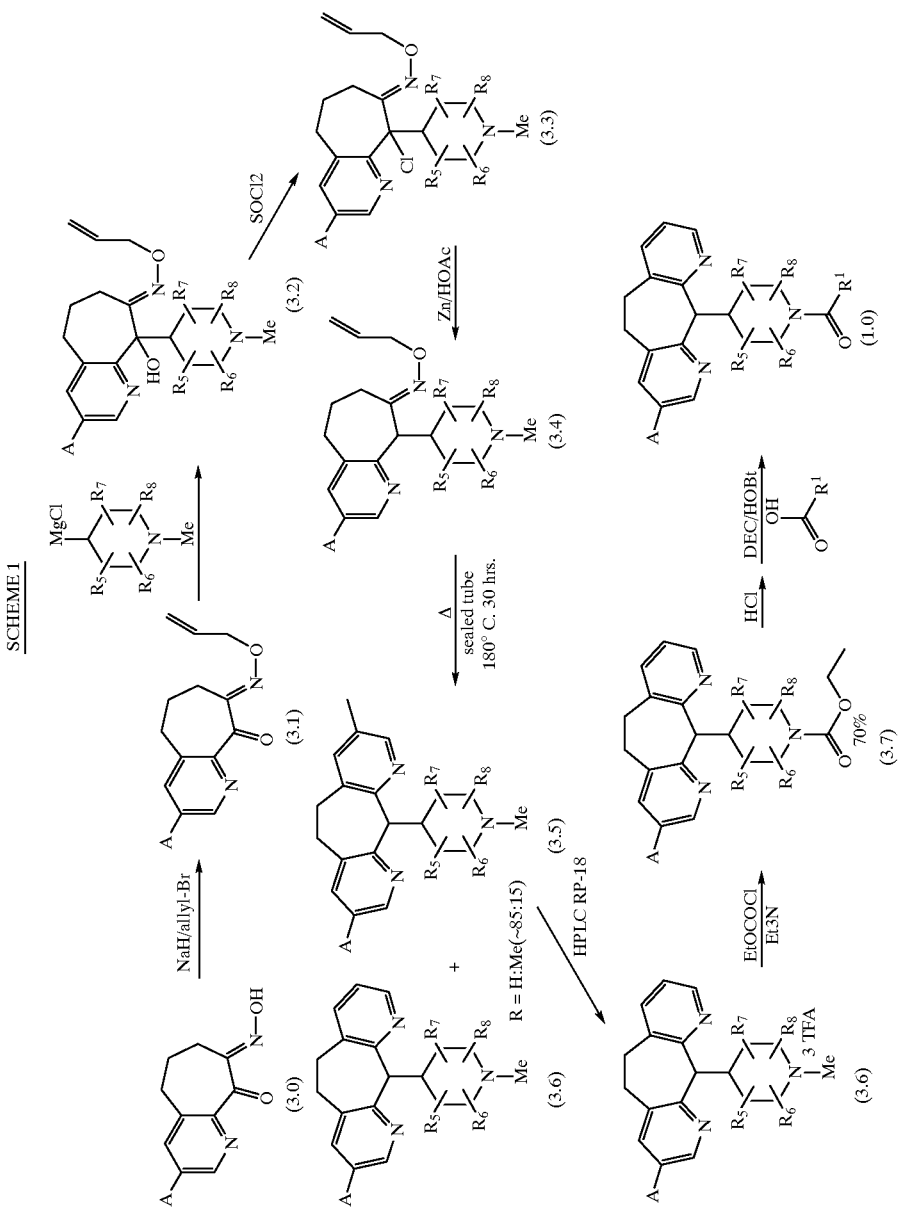

Scheme 2 shows the formation of compound (1.0) wherein the compound has the double bond. Compound (3.2) is dehydrated with a suitable base such as DBU at 60 to 150° C. for 1–18 hours to obtain compound (4.0). Compound (4.0) is then cyclized by sealing in a tube in the presence of air and heated to around 180° C. for 5–30 hours to obtain a mixture of the methyl compound (4.2) and compound (4.3). Compound (4.3) is obtained pure by chromatography on silica gel. Compound (4.3) is then demethylated by treatment with ethylchloroformate in the presence of a suitable base such as triethyl amine to form compound (4.4). Compound (4.4) is then treated with a suitable acid such as hydrochloric acid under reflux conditions for 5–24 hours and the solvent evaporated and the reaction mixture coupled with a suitable carboxylic acid containing the $R^1$ group using DEC and HOBt coupling conditions known to those skilled in the art to obtain compound (1.0). If compound (1.0) is desired with a methyl group, compound (4.2) can be subjected to the same conditions that compound (4.3) is subjected to and the reaction sequence can proceed as described above.

SCHEME 2

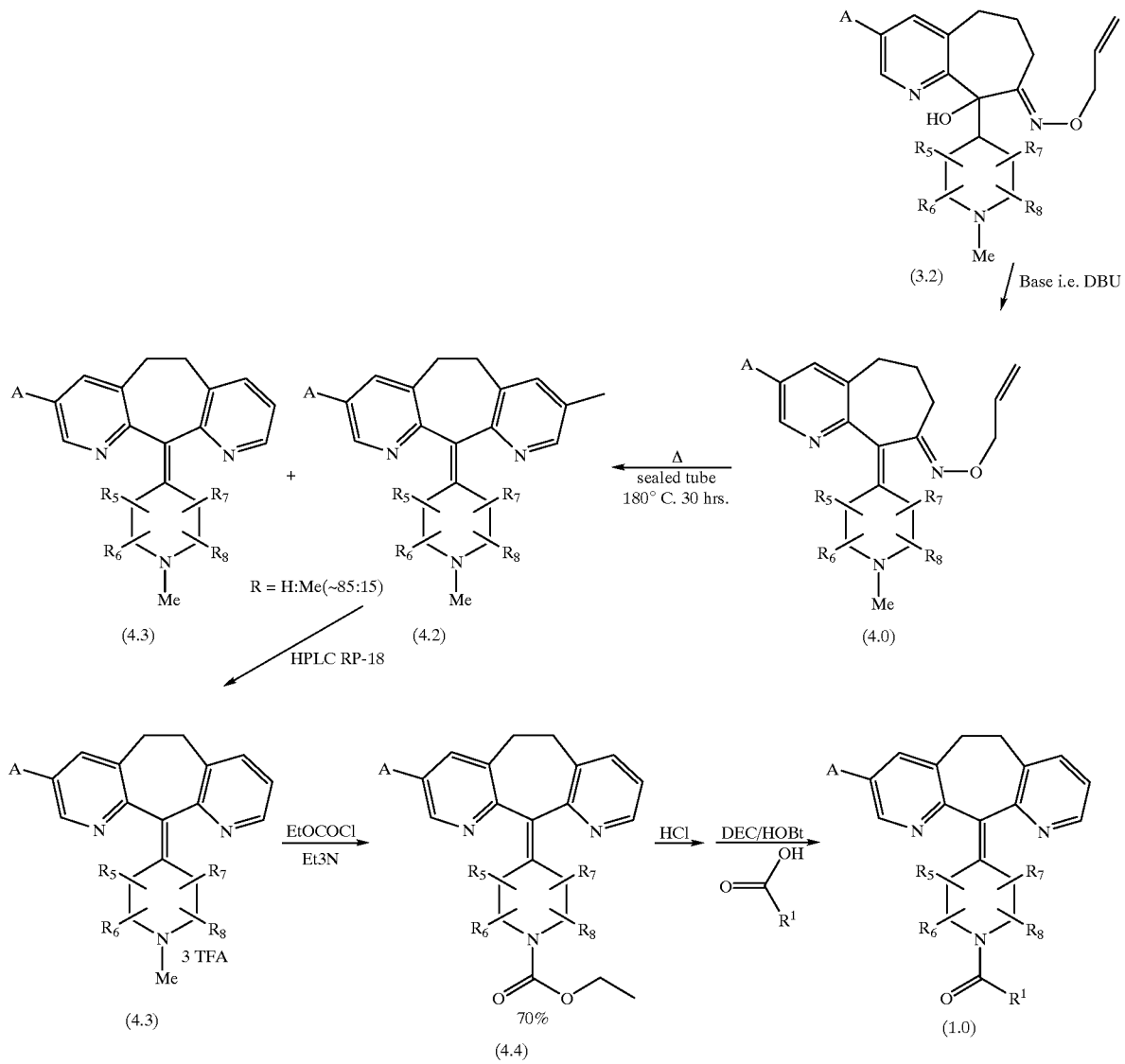

In schemes 1 and 2 above, compounds (3.6), (3.5), (4.2) and (4.3) are in the form of trifluoroacetic acid salts. The trifluoroacetic acid is removed when treated with the triethyl amine shown in schemes 1 and 2.

Scheme 3 shows the formation of compound (1.0) wherein A is halogen. Compound (5.0), with or without the double bond can be nitrated with one equivalent of a suitable nitrating agent such as tetrabutyl ammonium nitrate in the presence of trifluoroacetic anhydride to obtain the nitro compound (5.1). Compound (5.1) can then be reduced to the amine with a suitable reducing agent such as iron or catalytic hydrogenation in the presence of a palladium catalyst to obtain the amino compound (5.2). Compound (5.2) can then be brominated in the presence of a diazotizing agent such as sodium nitrite in the presence of bromine and hydrobomic acid to obtain the brominated compound (5.3). Compound (5.3) is then treated with a suitable acid such as hydrochloric acid under reflux conditions for 5–24 hours, the solvent evaporated, and the reaction mixture coupled with a suitable carboxylic acid containing the $R^1$ group using DEC and HOBt coupling conditions known to those skilled in the art to obtain compound (5.4).

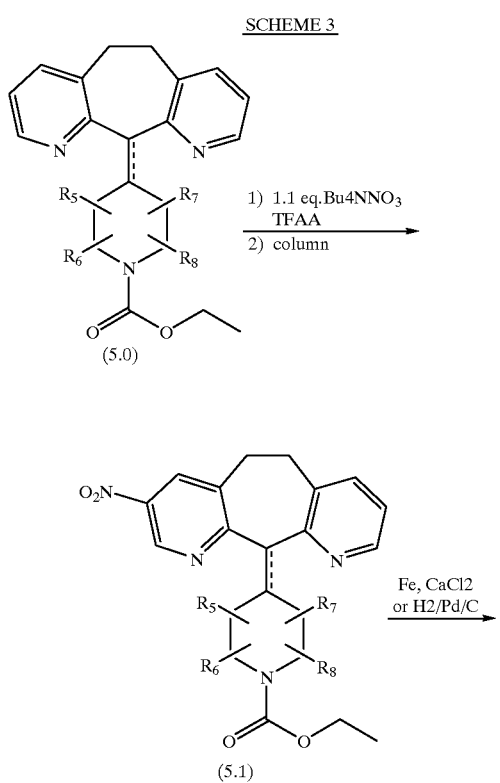

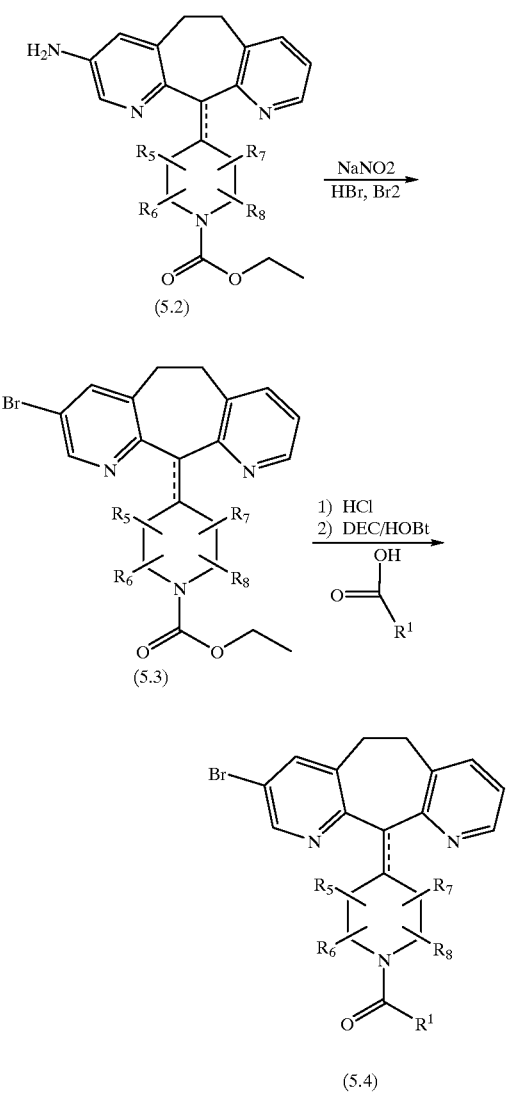

Scheme 4 shows the formation of compound (1.0) wherein A and B are halogen . Compound (5.0), with or without the double bond, can be nitrated with several equivalents of a suitable nitrating agent such as tetrabutyl ammonium nitrate in the presence of trifluoroacetic anhydride to obtain the nitro compound (6.0). Compound (6.0) can then be reduced to the amine with a suitable reducing agent such as iron or catalytic hydrogenation in the presence of a palladium catalyst to obtain the amino compound (6.1). Compound (6.1) can then be brominated in the presence of a diazotizing agent such as sodium nitrite in the presence of bromine and hydrobomic acid to obtain the dibrominated compound (6.2). Compound (6.2) can then be denitrated by treatment with Raney-Nickel in the presence of hydrogen. The de-nitrated compound is then treated with a suitable carboxylic acid containing the $R^1$ group using DEC and HOBt coupling conditions known to those skilled in the art to obtain compound (6.4).

SCHEME 4

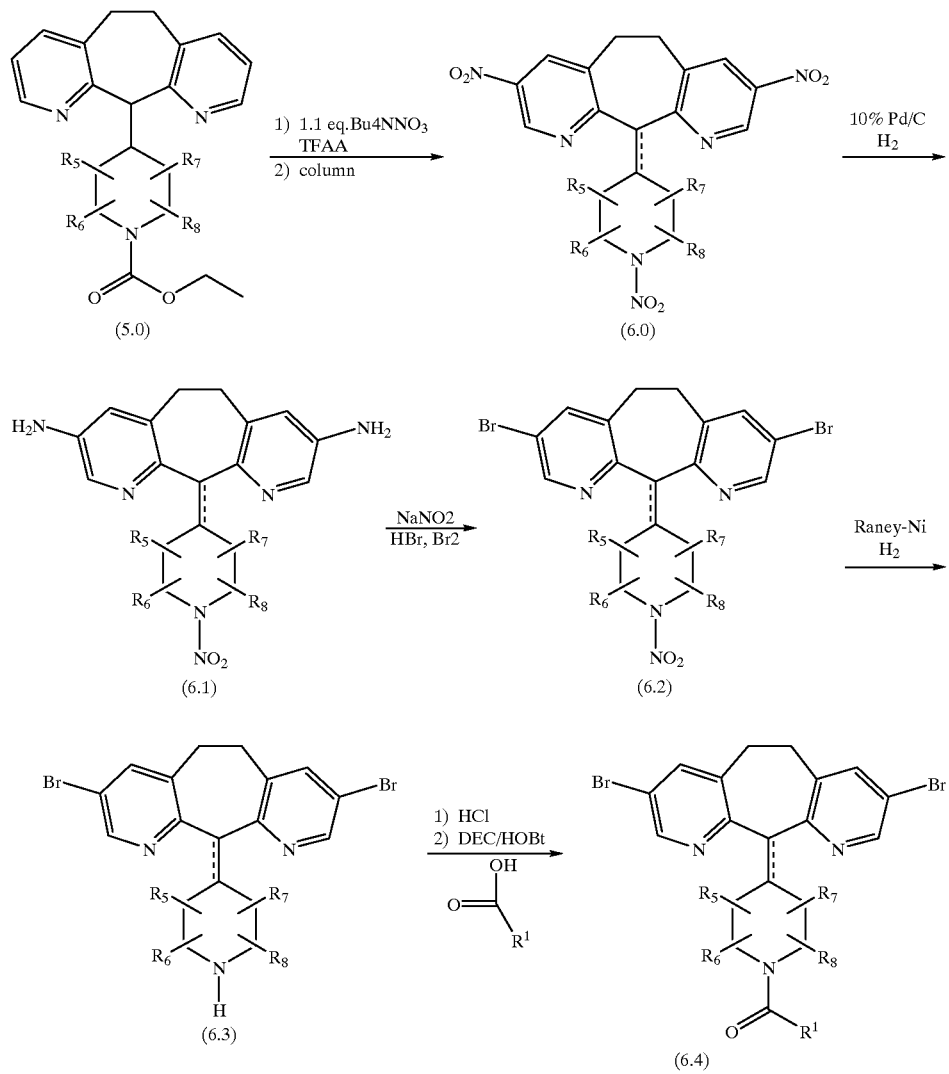

Scheme 5 shows the formation of compound (2.0), starting from compound (3.2), which may be prepared as shown in Scheme 1, above. Compound (3.2) is cyclized by sealing in a tube in the presence of air and heated to around 180° C. for 5–30 hours to obtain a mixture of the methyl compound (3.8a) and compound (3.8). Compound (3.8) is obtained pure by chromatography on silica gel. Compound (3.8) is then de-methylated by treatment with ethylchloroformate in the presence of a suitable base such as triethyl amine to form compound (3.9). Compound (3.9) is then treated with a suitable acid such as hydrochloric acid under reflux conditions for 5–24 hours and the solvent evaporated and the reaction mixture coupled with a suitable carboxylic acid containing the $R^1$ group using DEC and HOBt coupling conditions known to those skilled in the art to obtain compound (2.0).

Scheme 5

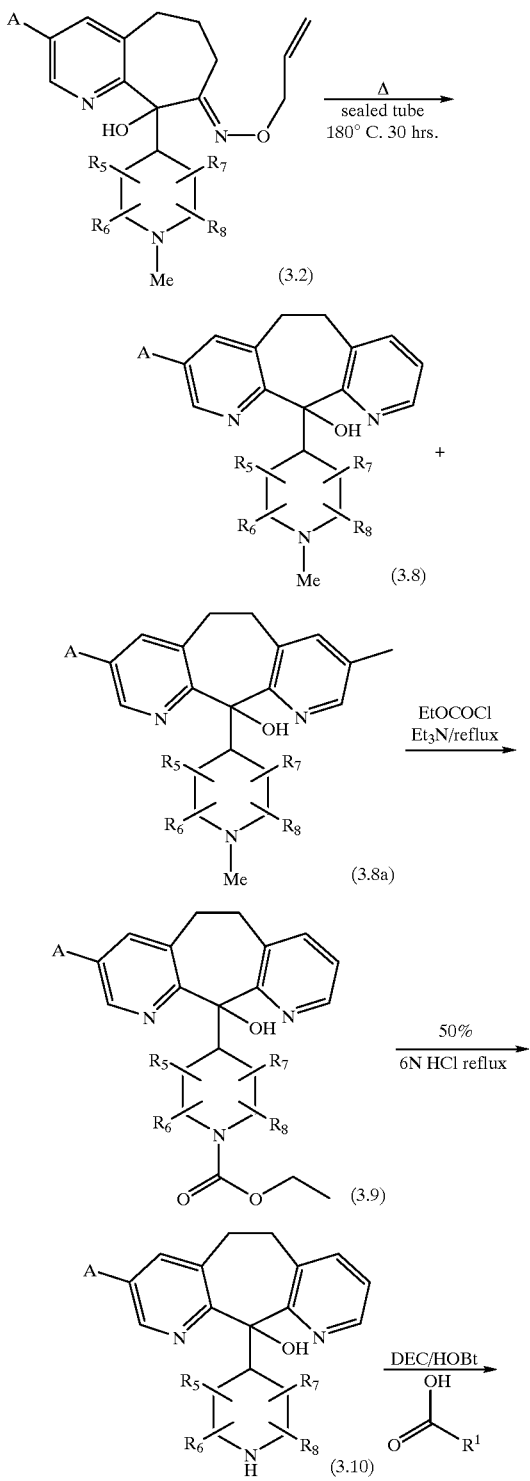

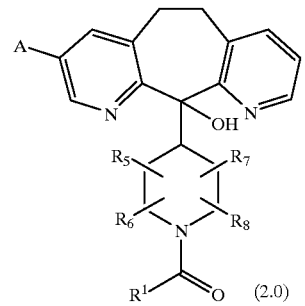

When R in Formula (1.0) or (2.0) is —C(O)NR$^1$R$^2$, —S(O)$_2$R$^1$, S(O)$_2$NR$^1$R$^2$ or —C(O)-OR$^1$, the compounds of the present invention may be made by subjecting compounds 3.7, 3.9, 5.3, or 6.3 to treatment with HCl to remove the EtOC(O)- group, thus forming an amine (i.e., the nitrogen on the piperidine ring is unsubstituted), followed by a conventional reaction to add the desired group. For example, when preparing compounds wherein R is —C(O)-NH—R$^G$, R$^G$ being an alkyl, cycloalkyl, or heterocycloalkyl group, after treatment with HCl, the resulting amine compound is reacted with an isocyanate of the formula RG—N=C=O, in a suitable solvent such as DMF, THF or CH$_2$Cl$_2$ using methods well known in the art. Alternatively, the amine is reacted with phosgene to form a chloroformate intermediate (i.e., the nitrogen on the piperidine ring is substituted with —C(O)Cl). The chloroformate is generally not isolated and is reacted with an amine of the formula R$^G$-NH$_2$, wherein R$^G$ is as defined above, to form a compound wherein R is —C(O)-NH—R$^G$.

When R is S(O)$_2$R$^1$, the amine can be dissolved in an appropriate solvent such as DMF of THF. A base is added such as triethylamine, and the appropriate alkylsulfonylchloride (R$^1$-S (O)$_2$Cl), prepared by methods known in the art, is added to the reaction mixture at 0° C. to ambient temperature with stirring. After 1–24 hours, the reaction mixture is added to water and the product extracted with a suitable solvent such as ethylacetate. The crude reaction product can then be chromatographed on a silica gel column.

When R is S(O)$_2$NR$^1$R$^2$, the amine can be dissolved in an appropriate solvent such as DMF of THF. A base is added such as triethylamine, and the appropriate alkylaminosulfonyl chloride (R$^1$R$^2$N—S(O)$_2$Cl), prepared by methods known in the art, is added to the reaction mixture at 0° C. to ambient temperature with stirring. After 1–24 hours, the reaction mixture is added to water and the product extracted with a suitable solvent such as ethylacetate. The crude reaction product can then be chromatographed on a silica gel column.

When R is —C(O)-OR$^1$, compounds 3.7, 3.9, 5.3 or 6.3 are treated with HCl to remove the EtOC(O)- group, followed by reaction with a suitably substituted chlorocarbonate to make the desired compound.

In the above processes, it is sometimes desirable and/or necessary to protect certain R5, R6, R7, R8 groups during the reactions. Conventional protecting groups are operable as described in Greene, T. W, "Protective Groups In Organic Synthesis," John Wiley & Sons, New York, 1981. The protecting groups may then be removed by conventional procedures.

Compounds useful in this invention are exemplified by the following examples, which should not be construed to limit the scope of the disclosure.

EXAMPLE 1

Preparation of 6,7-dihydro-5H-cyclohepta[b]pyridin-8,9-dione-8-oxime-o-allylether

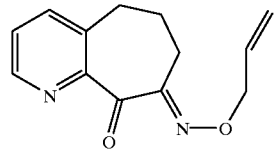

6,7-dihydro-5H-cyclohepta[b]pyridin-8,9-dione-8-oxime (10 gm, 52.58 mmol) was suspended in 100 ml of dry N,N-dimethylformamide (DMF) under a dry nitrogen atmosphere. Sodium hydride (60% oil dispersion, 1.388 gm, 57.83 mmol) was added portionwise over 15 minutes to the stirred mixture at 0° C. Allylbromide (8.4 ml) was added dropwise over 30 minutes. After the addition was over the mixture was stirred at ambient temperature for 18 hours. The DMF was concentrated to approximately 25 ml under high vacuum and diluted with 500 ml of methylenechloride. The mixture was washed with water two times, dried over magnesium sulfate, filtered and the solvent evaporated to obtain a gum which was chromatographed on a silica gel column using 25%–50% ethylacetate/hexanes as the eluent to obtain 5.7 gm, 47% of the title product. FABMS (M+1)=231

EXAMPLE 2

Preparation of 5,6,7,9-tetrahydro-9-hydroxy-9-(1-methyl-4-piperidinyl)-8H-cyclohepta [b]pyridin-8-one 0-(2-propenyl)oxime-o-allyl ether

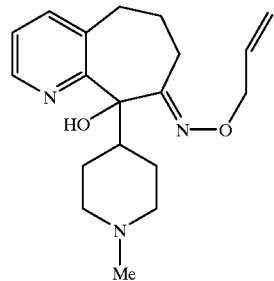

6,7-dihydro-5H-cyclohepta[b]pyridin-8,9-dione-8-oxime-o-allylether (10.13 gm, 44 mmol) was dissolved in 150 ml of dry THF under nitrogen atmosphere and cooled to 0° C. in an ice bath. While stirring, 88 ml of a 1 molar THF solution of N-methylpiperidine-4-magnesiumchloride was added dropwise. After evidence of reaction completion by TLC~1 hour, the reaction mixture was added to 500 ml of saturated ammonium chloride solution and extracted with 3×500 ml of ethylacetate. The ethylacetate layer was dried over magnesium chloride, filtered and evaporated to drynes under reduced pressure to obtain a crude oil which was chromatographed on silica gel using 2.5%–5% methanol/methylenechloride as the eluent to obtain 4.82 gm of title product. FABMS (M+1)=330

EXAMPLE 3

Preparation of 5,6,7,9-tetrahydro-9-chloro-9-(1-methyl-4-piperidinyl)-8H-cyclohepta [b]pyridin-8-one 0-(2-propenyl)oxime-o-allyl ether

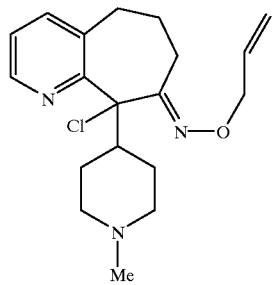

5,6,7,9-Tetrahydro-9-hydroxy-9-(1-methyl-4-piperidinyl)-8h-cyclohepta [b]pyridin-8-one 0-(2-propenyl) oxime (0.593 gm, 1.8 mmol) was dissolved in 10 ml of dry methylenechloride. Thionylchloride (0.428 gm, 3.6 mmol) was added dropwise and the reaction stirred at ambient temperature for 1 hour. The reaction mixture was carefully neutralized to pH 8–8.5 with saturated sodium bicarbonate solution, and the product extracted with methylenechloride, dried over magnesium sulfate, filtered, and evaporated to dryness to obtain a dark brown gum which was used in the next step without purification. FABMS (M+1)=348

EXAMPLE 4

Preparation of 5,6,7,9-tetrahydro-9-(1-methyl-4-piperidinyl)-8H-cyclohepta [b]pyridin-8-one 0-(2-propenyl)oxime-o-allylether

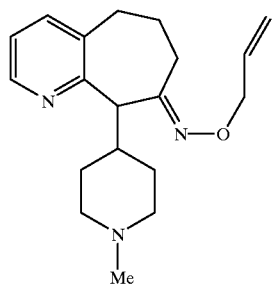

5,6,7,9-Tetrahydro-9-chloro-9-(1-methyl-4-piperidinyl)-8h-cyclohepta [b]pyridin-8-one 0-(2-propenyl)oxime (2.36 gm, 6.8 mmol) was dissolved in 50 ml of glacial acetic acid under a dry nitrogen atmosphere. Zinc (1.77 gm, 27.2 mmol) was added and the reaction mixture refluxed for 2 hours. The acetic acid was evaporated under high vacuum and the residue dissolved in methylenechloride and filtered. The methylenechloride solution was washed with brine, and evaporated to dryness to obtain a gum which was chromatographed on silica gel using 2.5%–5% methanol/methylenechloride as the eluent to obtain 2.03 gm of title product. FABMS (M+1)=314

EXAMPLE 5

Preparation of n-methyl-4-(6,11-dihydro-5H-cyclohepta [2,1-b:4,5-b']dipyridin-11-yl)-1-piperidine and n-methyl-4-(6,11-dihydro-8-methyl-5H-cyclohepta[2,1-b:4,5-b']dipyridin-11-yl)-1-piperidine

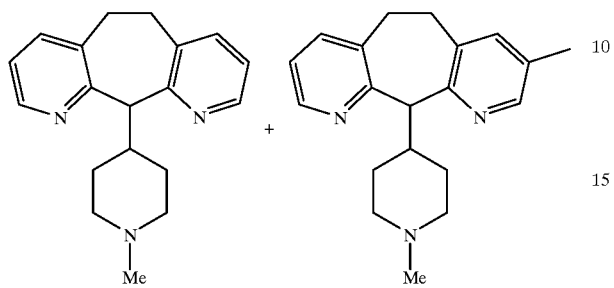

5,6,7,9-Tetrahydro-9-(1-methyl-4-piperidinyl)-8H-cyclohepta [b]pyridin-8-one 0-(2-propenyl)oxime-o-allylether (2 gm, 6.4 mmol) was placed in a pressure tube, sealed in the presence of air, and heated to 180° C. for 7 hours. The reaction mixture was allowed to cool to ambient temperature, and the brown residue chromatographed on silica gel using 2.5%–5% methanol/methylenechloride as the eluent to obtain 1 gm of N-METHYL-4-(6, 11-dihydro-5h-cyclohepta[2,1-b:4,5-b']dipyridin-11-yl)-1-piperidine and 0.1 gm of n-methyl-4-(6,11-dihydro-8-methyl-5h-cyclohepta [2,1-b:4,5-b']dipyridin-11-yl)-1-piperidine. FABMS (M+1)=294 and 308 respectively

EXAMPLE 6

Preparation of ethyl 4-(6,11-dihydro-5H-cyclohepta [2,1-b:4, 5-b']dipyridin-11-yl)-1-piperidinecarboxylate

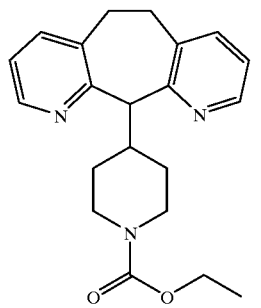

n-methyl- 4-(6,11-dihydro-5h-cyclohepta[2,1 -b:4,5-b'] dipyridin-11-yl)-1-piperidine (0.5 gm, 0.787 mmol) was suspended in 15 ml of dry toluene under a dry nitrogen atmosphere and heated to reflux. A solution of triethylamine (0.77 ml, 5.5 mmol) and ethylchloroformate (0.6 ml, 6.3 mmol) was added and the reaction refluxed for 3 hours. The reaction mixture was cooled to ambient temperature, ethylacetate added, and washed with 50 ml of 1 N sodium hydroxide solution. The aqueous layer was washed three times with ethylacetate. The organic layers were dried over magnesium sulfate, filtered and evaporated to dryness and chromatographed on silica gel using 2.5%–5% methanol/methylenechloride as the eluent to obtain 0.19 gm of title product. FABMS (M+1)=352

EXAMPLE 7

Preparation of ethyl 4-(6,11-dihydro-5H-cyclohepta [2,1-b:4,5-b']dipyridin-11-yl)-1-piperidine

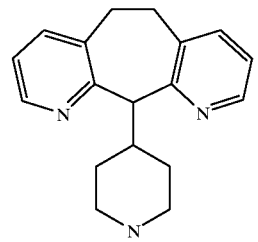

Ethyl 4-(6,11-dihydro-5H-cyclohepta[2,1-b:4,5-b'] dipyridin-11-yl)-1-piperidinecarboxylate (0.16 gm, 0.45 mmol) was dissolved in 10 ml of concentrated hydrochloric acid and refluxed for 18 hours. The reaction mixture was evaporated to obtain the title product as the hydrochloride salt. FABMS (M+1)=280

EXAMPLE 8

Preparation of 4-(6,11-dihydro-5H-cyclohepta[2,1-b:4,5-b']dipyridin-11-yl)-1-(4-pyridinylacetyl) n1-oxide piperidine

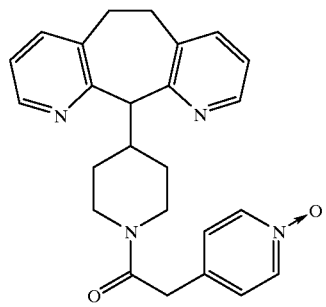

4-(6,11 -Dihydro-5H-cyclohepta[2,1-b:4,5-b']dipyridin-11 -yl)-1-piperidine (0.117 gm, 0.3 mmol) was dissolved in 10 ml of dry DMF. 1-(3-dimethylaminopropyl)-3-ethylcarbodiimide hydrochloride (DEC) (0.086 gm, 0.45 mmol), 1-hydroxybenzotriazole (HOBt) (0.061 gm, 0.45 mmol), N-methylmorpholine (0.33 ml, 3 mmol), and pyridy-lacetic acid-N-oxide (0.069 gm, 0.45 mmol) were added and the reaction mixture stirred at ambient temperature for 24 hours. The reaction mixture was added to brine and the product extracted with ethylacetate. The ethylacetate layers were dried over magnesium sulfate and evaporated under vacuo . The crude product was chromatographed on a silica column using 20% methanol-2 M ammonia/ methylenechloride to obtain 0.085 gm of title product. FABMS (M+1)=429

EXAMPLE 9

Preparation of 4-(6,11-dihydro-5H-cyclohepta[2,1-b:4,5-b']-3,8-dinitro-dipyridin-11-yl)-1-nitropiperidine

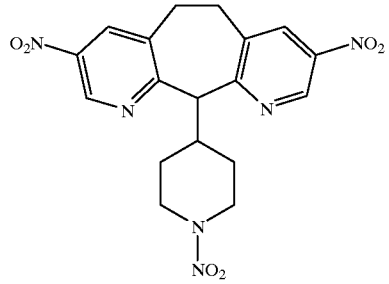

Ethyl 4-(6,11-dihydro-5H-cyclohepta[2,1-b:4,5-b']dipyridin-11-yl)-1-piperidinecarboxylate (0.562 gm, 1.6 mmol) was dissolved in dichloromethane and cooled to 0° C. in an ice bath. Tetrabutyl-ammonium nitrate (2.43 gm, 8.0 mmol) was added and trifluoroacetic anhydride (1.13 ml, 8.0 mmol) was added dropwise and the reaction mixture stirred fro 2 hours and then at ambient temperature for 18 hours. The reaction mixture was basified to pH 10–11 with 10% sodium hydroxide and the product extracted with dichloromethane three times. The dichloromethane layers were combined and dried over magnesium sulfate, filtered and evaporated to dryness. The residue was chromatographed on silica gel using 25%–75% ethylacetate/hexanes as the eluent to obtain 0.41 gm of the title product as a brown solid. FABMS (M+1)=416

EXAMPLE 10

Preparation of 4-(6,11-dihydro-5H-cyclohepta[2,1-b:4,5-b']-3,8-diamino-dipyridin-11-yl)-1-nitropiperidine

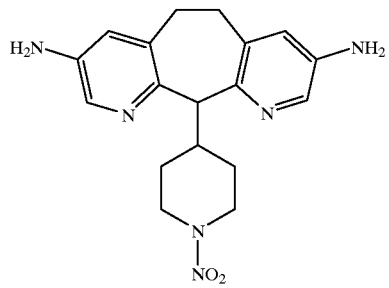

4-(6,11-Dihydro-5H-cyclohepta[2,1-b:4,5-b']-3,8-dinitro-dipyridin-11-yl)-1-nitropiperidine (0.4 gm 0.97 mmol) was dissolved in 50 ml of 200 proof ethanol. 0.1 gm of 10% palladium on carbon was added and the mixture hydrogenated at 50 psi for 18 hours. The catalyst was filtered and the ethanol evaporated to obtain a brown gum. The crude product was chromatographed on silica gel using 2.5 % methanol/dichloromethane as eluent to obtain 0.113 gm of title product. FABMS (M+1)=356

EXAMPLE 11

Preparation of 4-(6,11-dihydro-5H-cyclohepta[2,1-b:4,5-b']-3,8-dibromo-dipyridin-11-yl)-1-nitropiperidine

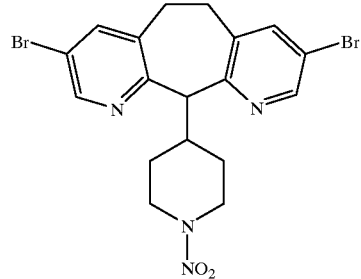

4-(6,11-Dihydro-5H-cyclohepta[2,1-b:4,5-b']-3,8-diamino-dipyridin-11-yl)-1-nitropiperidine (0.099 gm, 0.28 mmol) was dissolved in 16 ml of 48% hydrobromic acid. The reaction mixture was cooled to 0° C. in an ice bath and bromine (0.16 ml, 3.08 mmol) was added dropwise. The reaction mixture was stirred for 15 minutes and a solution of sodium nitrite ( 0.116 gm, 1.68 mmol) in 2 ml of water was added dropwise and the mixture stirred for 4 hours. The reaction mixture was then basified to pH 10–11 with 50% sodium hydroxide and the product extracted into dichloromethane, dried over magnesium sulfate, filtered, and evaporated to dryness. The crude product was chromatographed on silica gel using 25% ethylacetatelhexanes as the eluent to obtain 0.04 gm of the title product. FABMS (M+1)=482

EXAMPLE 12

Preparation of 4-(6,11-dihydro-5H-cyclohepta[2,1-b:4,5-b']-3,8-dibromo-dipyridin-11-yl)-piperidine

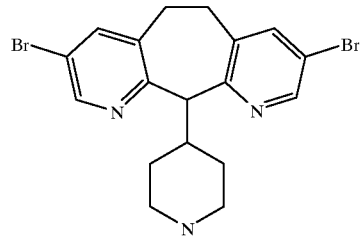

4-(6,11-Dihydro-5H-cyclohepta[2,1-b:4,5-b']-3,8-dibromo-dipyridin-11-yl)-1-nitropiperidine (0.035 gm, 0.073 mmol) was dissolved in absolute ethanol and 20 mg of Raney-Ni was added and the mixture hydrogenated at 50 psi of hydrogen. After 8 hours, the Raney-Ni was filtered and the solvent evaporated to obtain the title compound. FABMS (M+1)=437

EXAMPLE 13

Preparation of 4-(3,8-dibromo-6,11-dihydro-5H-cyclohepta [2,1-b:4,5-b']dipyridin-11-yl)-1-(4-pyridinylacetyl) n1-oxide piperidine

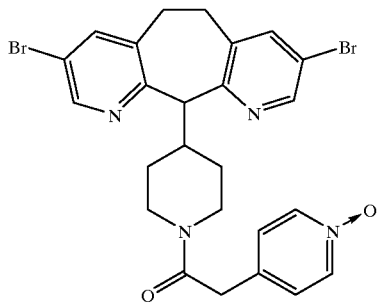

4-(3,8-DIbromo-6,11-dihydro-5H-cyclohepta[2,1-b:4,5-b']dipyridin-11-yl)-1-(4-pyridinylacetyl) n1-oxide piperidine was prepared as in procedure 8 utilizing 4-(6,11-dihydro-5H-cyclohepta [2,1-b:4,5-b']-3,8-dibromo-dipyridin-11-yl)-piperidine as the starting material. FABMS (M+1)=586

EXAMPLE 14

Preparation of ethyl 4-(3-nitro-6,11-dihydro-5H-cyclohepta [2,1-b:4,5-b']dipyridin-11-yl)-1-piperidinecarboxylate

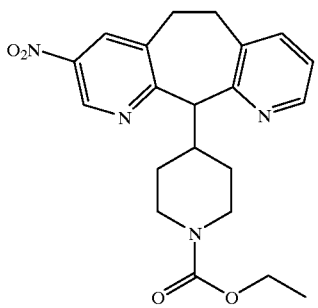

Ethyl 4-(6,11-dihydro-5H-cyclohepta[2,1-b:4,5-b']dipyridin-11-yl)-1-piperidinecarboxylate (0.512 gm, 1.46 mmol) was dissolved in 20 ml of dry dichloromethane at 0° C. Tetrabutyl-ammoniumnitrate (0.489 gm, 1.6 mmol) was added and trifluoroacetic anhydride (0.227 ml, 1.6 mmol) was added dropwise. The reaction mixture was stirred for 2 hours and then allowed to warm to ambient temperature and stirred for 18 hours. The reaction mixture was basified to pH 10 with 1 N sodium hydroxide, and the product extracted with 3×100 ml of dichloromethane and dried over magnesium sulfate and filtered. The dichloromethane was evaporated and the residue chromatographed on silica gel using 25% to 75% ethylacetate/hexanes as the eluent to obtain 0.16 gm of title product. FABMS (M+1)=397

EXAMPLE 15

Preparation of ethyl 4-(3-amino-6,11-dihydro-5H-cyclohepta [2,1-b:4,5-b']dipyridin-11-yl)-1-piperidinecarboxylate

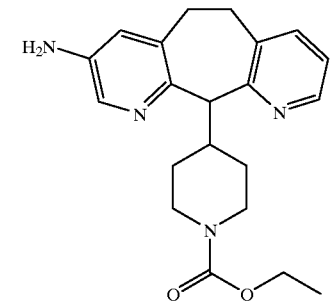

Ethyl 4-(3-nitro-6,11-dihydro-5H-cyclohepta[2,1-b:4,5-b']dipyridin-11-yl)-1-piperidinecarboxylate (0.14gm, 0.367 mmol) was dissolved in 15 ml of ethanol. Palladium/carbon (10%, 20 mg) was added and the reaction mixture hydrogenated at 50 psi of hydrogen for 2 hours. The palladium was filtered and the ethanol evaporated to give 0.12 gm of the title product. FABMS (M+1)=367

EXAMPLE 16

Preparation of ethyl 4-(3-bromo-6,11-dihydro-5H-cyclohepta [2,1-b:4,5-b']dipyridin-11-yl)-1-piperidinecarboxylate

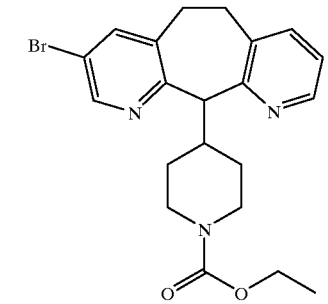

Ethyl 4-(3-amino-6,11-dihydro-5H-cyclohepta[2,1-b:4,5-b']dipyridin-11-yl)-1-piperidinecarboxylate (0.05 gm, 0.136 mmol) was dissolved in 4 ml of 48% hydrobromic acid. The reaction mixture was cooled to 0° C. and bromine (0.038 ml, 0.738 mmol) was added dropwise and stirred for 15 minutes. Sodium nitrite (0.028 gm, 0.408 mmol) was added, as a solution in 0.5 ml of water, dropwise over 15 minutes. The reaction was stirred at 0° C. for 3–4 hours. The reaction mixture was basified to pH 10 with 10% sodium hydroxide and the produt extracted into ethylacetate. The ethylacetate layer was dried over magnesium sulfate, filtered and evaporated to dryness. The crude product was chromatographed on silica gel using 10–20% methanol/dichoromethane as the eluent to obtain 0.035 gm of title product. FABMS (M+1)=431

EXAMPLE 17

Preparation of 4-(3-bromo-6,11-dihydro-5H-cyclohepta [2,1-b:4,5-b']dipyridin-11-yl)-1-(4-pyridinylacetyl) n1-oxide piperidine

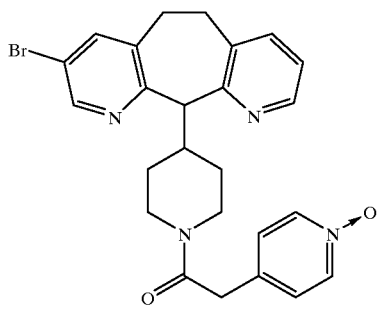

4-(3-Bromo-6,11-dihydro-5H-cyclohepta[2,1-b:4,5-b']dipyridin-11-yl )-1-(4-pyridinylacetyl) n1-oxide piperidine was prepared utilizing procedures 7–8 starting with ethyl 4-(3-bromo-6,11-dihydro-5H-cyclohepta [2,1-b:4,5-b']dipyridin-11-yl)-1-piperidinecarboxylate. FABMS (M+1)= 507

EXAMPLE 18

Preparation of 4-(3-methyl-6,11-dihydro-5H-cyclohepta [2,1-b:4,5-b']dipyridin-11-yl)-1-(4-pyridinylacetyl) n1-oxide piperidine

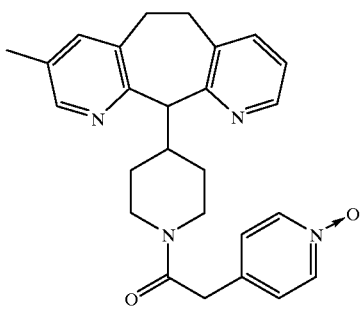

4-(3-Methyl-6,11-dihydro-5h-cyclohepta[2,1-b:4,5-b'] dipyridin-11 -yl)-1-(4-pyridinylacetyl) n1-oxide piperidine was prepared utilizing procedure 6–8 above starting with n-methyl-4-(6,11-dihydro-8-methyl-5H-cyclohepta [2,1-b:4,5-b']dipyridin-11-yl)-1-piperidine. FABMS (M+1)=443

EXAMPLE 19

Preparation of n-methyl-4-(6,11-hydroxy-5H-cyclohepta [2,1-b:4,5-b']dipyridin-11-yl)-1-piperidine and n-methyl-4-(6,11-hydroxy-8-methyl-5H-cyclohepta[2,1-b:4,5-b']dipyridin-11-yl)-1-piperidine

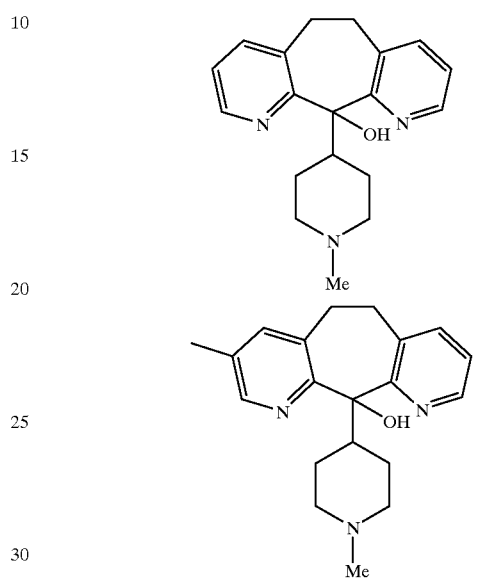

Follow procedure as in Example 5 substituting 5,6,7,9-Tetrahydro-9-hydroxy-9-( 1-methyl-4-piperidinyl)-8H-cyclohepta[b]pyridin-8-one 0-(2-propenyl)oxime-o-allylether for 5,6,7,9-Tetrahydro-9-(1-methyl-4-piperidinyl)-8H-cyclohepta[b]pyridin-8-one 0-(2-propenyl) oxime-o-allylether to obtain the title compound in 11% yield. FABMS (M+1)=310 and 324 respectively.

EXAMPLE 20

Preparation of ethyl 4-(6,11-hydroxy-5H-cyclohepta [2,1-b:4,5-b']dipyridin-11-yl)-1-piperidine

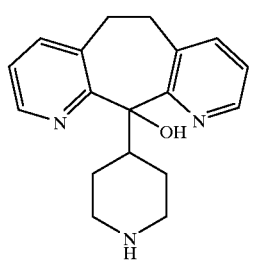

Follow procedure as in Examples 6 and 7 using n-methyl-4-(6,11 -hydroxy-5H-cyclohepta [2,1-b:4,5-b']dipyridin-11-yl)-1-piperidine to obtain the title compound which was utitlized directly in the next step.

EXAMPLE 21

Preparation of 4-(6,11-hydroxy-5H-cyclohepta[2,1-b:4,5-b']dipyridin-11-yl)-1(4-pyridinylacetyl) n1-oxide piperidine

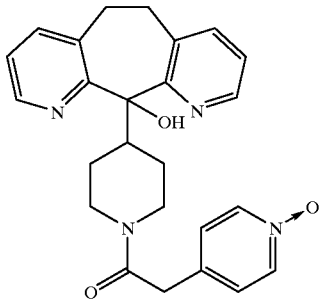

Follow procedure as in Example 8 using ethyl 4-(6,11-hydroxy-5H-cyclohepta [2,1-b:4,5-b']dipyridin-11-yl)-1-piperidine to obtain the title compound in 13% yield. FABMS (M+1)=431

ASSAYS

FPT $IC_{50}$ (inhibition of farnesyl protein transferase, in vitro enzyme assay) and COS Cell $IC_{50}$ (Cell-Based Assay) were determined following the assay procedures described in WO 95/10516, published Apr. 20, 1995. GGPT $IC_{50}$ (inhibition of geranylgeranyl protein transferase, in vitro enzyme assay), Cell Mat Assay, and anti-tumor activity (in vivo anti-tumor studies) could be determined by the assay procedures described in WO 95/10516. The disclosure of WO 95/10516 is incorporated herein by reference thereto.

Additional assays can be carried out by following essentially the same procedure as described above, but with substitution of alternative indicator tumor cell lines in place of the T24-BAG cells. The assays can be conducted using either DLD-1-BAG human colon carcinoma cells expressing an activated K-ras gene or SW620-BAG human colon carcinoma cells expressing an activated K-ras gene. Using other tumor cell lines known in the art, the activity of the compounds of this invention against other types of cancer cells could be demonstrated.

Soft Agar Assay:

Anchorage-independent growth is a characteristic of tumorigenic cell lines. Human tumor cells are suspended in growth medium containing 0.3% agarose and an indicated concentration of a farnesyl transferase inhibitor. The solution is overlayed onto growth medium solidified with 0.6% agarose containing the same concentration of farnesyl transferase inhibitor as the top layer. After the top layer is solidified, plates are incubated for 10–16 days at 37° C. under 5% $CO_2$ to allow colony outgrowth. After incubation, the colonies are stained by overlaying the agar with a solution of MTT (3-[4,5-dimethyl-thiazol-2-yl ]-2,5-diphenyltetrazolium bromide, Thiazolyl blue) (1 mg/mL in PBS). Colonies can be counted and the $IC_{50}$'s can be determined.

The results are given in the table below ("uM" represents micromolar).

| Compound of Example No. | FPT $IC_{50}$ ($\mu$M) | COS Cell $IC_{50}$ ($\mu$M) |
|---|---|---|
| 6 | >17.0 | |
| 8 | 25% @> 1.4 | |
| 13 | 0.028 | 0.125 |
| 17 | 0.29 | |
| 18 | 0.16 | |

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, more preferably from about 1 mg. to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen is oral administration of from 10 mg to 2000 mg/day preferably 10 to 1000 mg/day, in two to four divided doses to block tumor growth.

The compounds are non-toxic when administered within this dosage range.

The compounds of the present invention are also useful as antihistamines. They act as anti-allergic agents in the treatment of conditions such as perennial and seasonal allergic rhinitis and chronic urticaria. Thus, an effective amount of a compound of the present invention may be administered to an animal to effect an anti-allergic response. Although the required dosage for an anti-allergic response will be determined by such factors as the patient's age, sex, weight, and the severity of the allergic reaction to be treated, the preferred human dosage range is preferably from 1 to 1,000 mg/day. The preferred dosage ranges for other animals can readily be determined by using standard testing methods.

The following are examples of pharmaceutical dosage forms which contain a compound of the invention. The scope of the invention in its pharmaceutical composition aspect is not to be limited by the examples provided.

PHARMACEUTICAL DOSAGE FORM EXAMPLES

Example A

| | Tablets | | |
|---|---|---|---|
| No. | Ingredients | mg/tablet | mg/tablet |
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
| | Total | 300 | 700 |

METHOD OF MANUFACTURE

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

Example B

| | Capsules | | |
|---|---|---|---|
| No. | Ingredient | mg/capsule | mg/capsule |
| 1. | Active compound | 100 | 500 |
| 2. | Lactose USP | 106 | 123 |
| 3. | Corn Starch, Food Grade | 40 | 70 |
| 4. | Magnesium Stearate, NF | 7 | 7 |
| | Total | 253 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound having the formula:

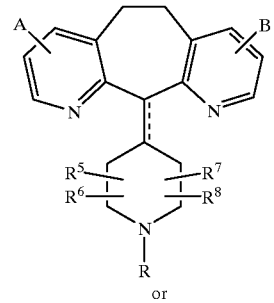

(1.0)

or

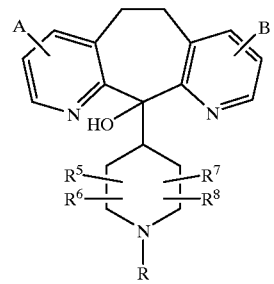

(2.0)

or a pharmaceutically acceptable salt or solvate thereof, wherein:

A is alkyl, halo or H;

B is methyl, halo or H;

the dotted line represents an optional double bond;

$R^5$, $R^6$, $R^7$ and $R^8$ are independently selected from the group consisting of H, —$CF_3$, —$COR^{10}$, alkyl or aryl, said alkyl or aryl optionally being substituted with —$OR^{10}$, —$SR^{10}$, —$S(O)_tR^{11}$, wherein t is 0, 1 or 2, —$NR^{10}COOR^{11}$, —$N(R^{10})_2$, —$NO_2$, —$COR^{10}$, —$OCOR^{10}$, —$OCO_2R^{11}$, —$CO_2R^{10}$ or $OPO_3R^{10}$ or $R^5$ is combined with $R^6$ to represent =O or =S and/or $R^7$ is combined with $R^8$ to represent =O or =S;

$R^{10}$ represents H, alkyl, aryl, or aralkyl;

$R^{11}$ represents alkyl or aryl;

R is —C(O)$R^1$, —C(O)-O$R^1$, —C(O)N$R^1R^2$, —S(O)$_2$-$R^1$, and —S(O)$_2$N$R^1R^2$ wherein $R^1$ and $R^2$ are independently selected from the group consisting of H, alkyl, aryl, arylalkyl, heteroaryl, heteroarylalkyl, C3–C6 cycloalkyl, cycloalkylalkyl, heterocycloalkyl, substituted alkyl, substituted aryl, substituted arylalkyl, substituted heteroaryl, substituted heteroarylalkyl, substituted (C3–C6) cycloalkyl, substituted cycloalkylalkyl, substituted heterocycloalkyl, wherein said substituted groups have one or more substituents selected from: $C_1$–$C_6$ alkyl, alkoxy, aralkyl, heteroarylalkyl, —NO$_2$, alkyloxyalkyl, alkyloxyalkyloxyalkyl, $C_3$–$C_6$ cycloalkyl, aryl, —CN, heteroaryl, heterocycloalkyl, =O, —OH, amino, substituted amino, nitro and halo, with the proviso that $R^1$ is not H for —C(O)-O$R^1$ or for —S(O)$^2R^1$.

2. The compound of claim 1 wherein A and B are independently selected from methyl or halo.

3. The compound of claim 1 wherein $R^5$, $R^6$, $R^7$ and $R^8$ are independently selected from the group consisting of H, —CF$_3$, alkyl, aryl, cycloalkyl and heterocycloalkyl.

4. The compound of claim 3, wherein R is —C(O)$R^1$.

5. The compound of claim 4, wherein $R^1$ is -(CH$_2$)$_n R^A$, wherein n is an integer from 0 to 6, and wherein $R^A$ is selected from aryl, cycloalkyl and heterocycloalkyl.

6. A method for inhibiting farnesyl protein transferase in a mammal in need thereof comprising administering to the mammal in need thereof a farnesyl protein transferase inhibiting amount of the compound of claim 1.

7. A method for effecting an anti-allergic response in a mammal in need thereof, comprising administering to the mammal an effective amount of the compound of claim 1.

8. A compound having the formula (1.0) or (2.0):

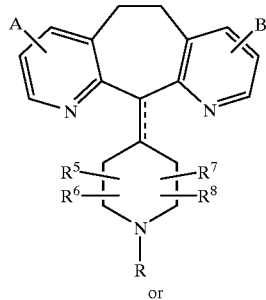

(1.0)

or

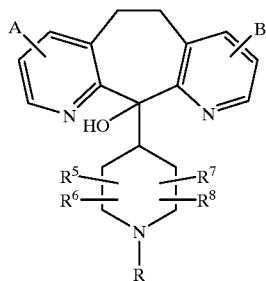

(2.0)

or a pharmaceutically acceptable salt or solvate thereof, wherein:

A is alkyl, halo or H;

B is methyl, halo or H;

the dotted line represents an optional double bond;

$R^5$, $R^6$, $R^7$ and $R^8$ are independently selected from the group consisting of H, —CF$_3$, —CO$R^{10}$, alkyl or aryl, the alkyl or aryl groups optionally being substituted with —O$R^{10}$, —S$R^{10}$, —S(O)$_tR^{11}$, wherein t is 0, 1 or 2, —N$R^{10}$COO$R^{11}$, —N($R^{10}$)$_2$, —NO$_2$, —CO$R^{10}$, —OCO$R^{10}$, —OCO$_2R^{10}$, —CO$_2R^{10}$ or OPO$_3R^{10}$ or $R^5$ is combined with $R^6$ to represent =O or =S and/or $R^7$ is combined with $R^8$ to represent =O or =S;

$R^{10}$ represents H, alkyl, aryl, or aralkyl;

$R^{11}$ represents alkyl or aryl;

R is —C(O)$R^1$ or —C(O)-O$R^1$, wherein $R^1$ is selected from the group consisting of H, alkyl, aryl, arylalkyl, heteroaryl, heteroarylalkyl, $C_3$–$C_6$ cycloalkyl, cycloalkylalkyl, heterocycloalkyl, substituted alky, substituted aryl, substituted arylalkyl, substituted heteroaryl, substituted heteroarylalkyl, substituted $C_3$–$C_6$ cycloalkyl, substituted cycloalkylalkyl and substituted heterocycloalkyl, wherein the substituted groups have one or more substituents selected from the group consisting of $C_1$–$C_6$ alkyl, alkoxy, aralkyl, heteroarylalkyl, —NO$_2$, alkyloxyalkyl, alkyloxyalkyloxyalkyl, $C_3$–$C_6$ cycloalkyl, aryl, —CN, heteroaryl, heterocycloalkyl, =O, —OH, amino, substituted amino and halo, with the proviso that $R^1$ is not H for —C(O)-O$R^1$.

9. The compound of claim 8, wherein A and B are independently selected from the group consisting of methyl and halo.

10. The compound of claim 8, wherein $R^1$ is an alkyl or alkylpyridine-N-oxide group.

11. The compound of claim 8, wherein R is:

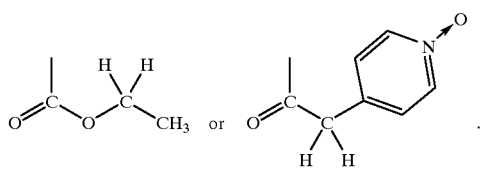

12. The compound of claim 11, wherein A and B are independently selected from the group consisting of —H, halo or methyl.

13. The compound of claim 12, wherein the halo substituent is a bromine atom.

14. The compound of claim 8, which is

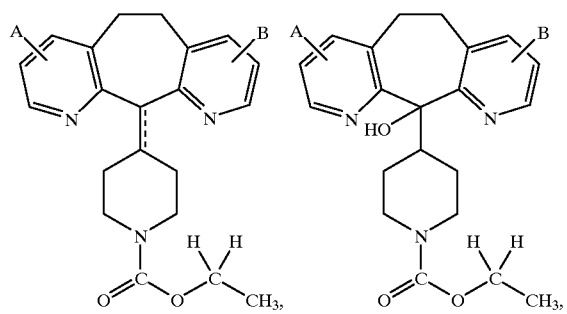

-continued
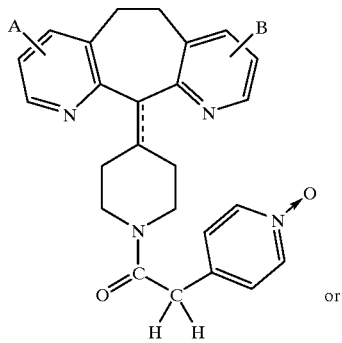
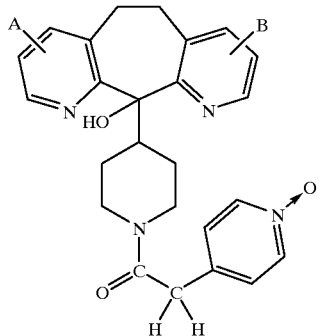
where A and B are defined as in claim 8.
15. The compound of claim 14, wherein A is —H, methyl or —Br and B is —H or —Br.
16. The compound of claim 15, which is:
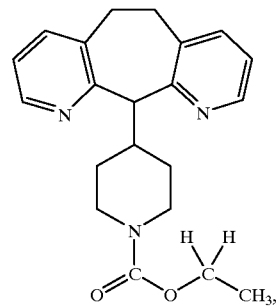
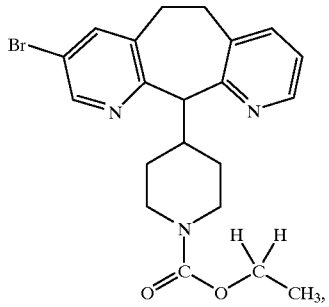
-continued
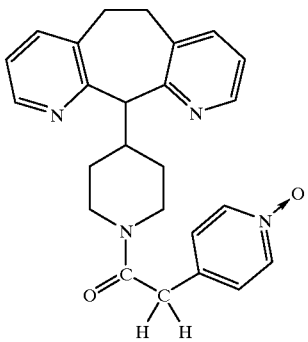
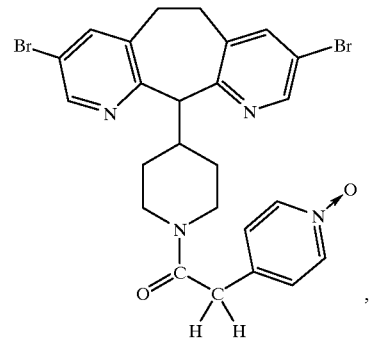
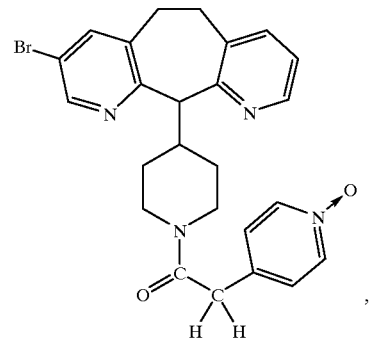
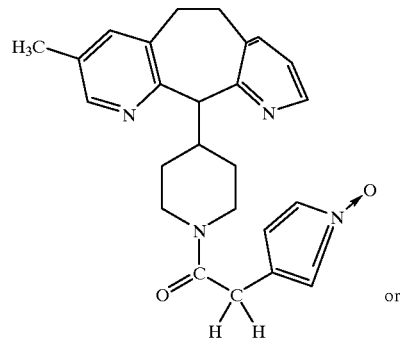
or

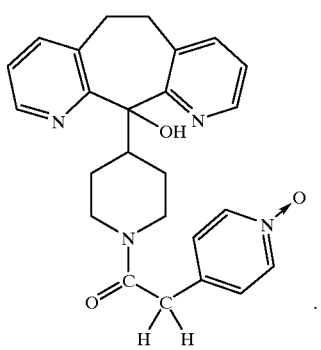

17. The compound of claim 16, which is:

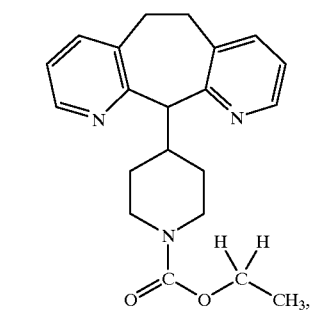

,

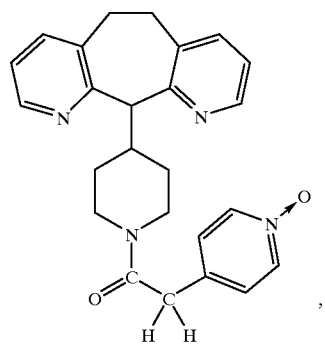

,

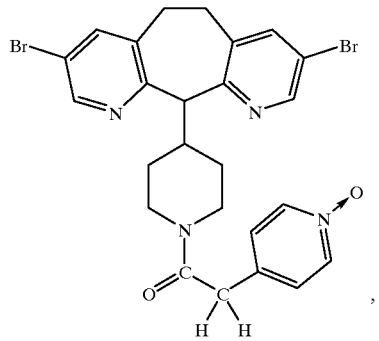

,

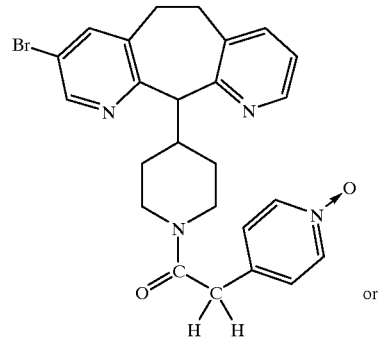

or

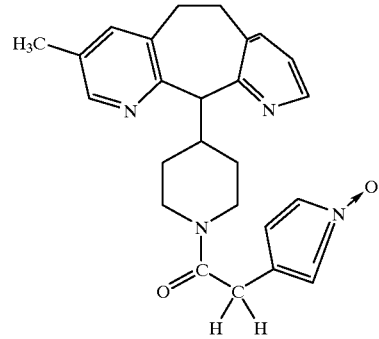

18. The compound of claim 17, which is:

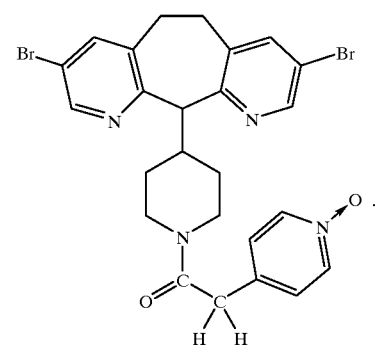

.

19. A method for inhibiting farnesyl protein transferase in a mammal in need thereof, comprising administering to the mammal in need thereof a farnesyl protein transferase inhibiting amount of the compound of claim 8.

20. A method for effecting an anti-allergic response in a mammal in need thereof, comprising administering to the mammal in need thereof an effective amount of the compound of claim 8.

* * * * *